(12) United States Patent
Kadowaki et al.

(10) Patent No.: US 9,795,721 B2
(45) Date of Patent: Oct. 24, 2017

(54) ANTITHROMBOTIC MATERIAL

(71) Applicant: Toray Industries, Inc., Tokyo (JP)

(72) Inventors: Koji Kadowaki, Otsu (JP); Masaki Fujita, Otsu (JP); Yuka Sakaguchi, Otsu (JP); Kazuhiro Tanahashi, Otsu (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 15/038,560

(22) PCT Filed: Nov. 27, 2014

(86) PCT No.: PCT/JP2014/081307
§ 371 (c)(1),
(2) Date: May 23, 2016

(87) PCT Pub. No.: WO2015/080177
PCT Pub. Date: Jun. 4, 2015

(65) Prior Publication Data
US 2016/0296679 A1 Oct. 13, 2016

(30) Foreign Application Priority Data

Nov. 28, 2013 (JP) ................................. 2013-246580
Dec. 24, 2013 (JP) ................................. 2013-265834

(51) Int. Cl.
*A61L 33/00* (2006.01)

(52) U.S. Cl.
CPC ....... *A61L 33/0041* (2013.01); *A61L 33/0076* (2013.01)

(58) Field of Classification Search
CPC .......................... A61L 33/0041; A61L 33/0076
See application file for complete search history.

(56) References Cited

U.S. PATENT DOCUMENTS

| | | | |
|---|---|---|---|
| 4,229,838 A | 10/1980 | Mano | |
| 5,529,986 A | 6/1996 | Larsson et al. | |
| 5,532,311 A | 7/1996 | Sirvio et al. | |
| 5,672,638 A * | 9/1997 | Verhoeven | A61L 33/0029 424/423 |
| 5,679,659 A | 10/1997 | Verhoeven et al. | |
| 5,866,113 A * | 2/1999 | Hendriks | A61L 27/22 424/486 |
| 6,053,939 A | 4/2000 | Okuda et al. | |
| 6,146,771 A | 11/2000 | Wirt et al. | |
| 6,461,665 B1 | 10/2002 | Scholander | |
| 2004/0213818 A1 | 10/2004 | Kashiwabara et al. | |
| 2011/0274744 A1 * | 11/2011 | Picart | A61L 15/28 424/445 |

FOREIGN PATENT DOCUMENTS

| | | |
|---|---|---|
| JP | 54-13694 A | 2/1979 |
| JP | 60-41947 B2 | 9/1985 |
| JP | 60-47287 B2 | 10/1985 |
| JP | 1-262869 A | 10/1989 |
| JP | 2-144070 A | 6/1990 |
| JP | 6-86808 A | 3/1994 |
| JP | 6-510783 A | 12/1994 |
| JP | 7-178161 A | 7/1995 |
| JP | 9-169801 A | 6/1997 |
| JP | 9-276394 A | 10/1997 |
| JP | 10-151192 A | 6/1998 |
| JP | 10-513074 A | 12/1998 |
| JP | 11-235381 A | 8/1999 |
| JP | 11-511355 A | 10/1999 |
| JP | 2002-514126 A | 5/2002 |
| JP | 3341503 B2 | 11/2002 |
| JP | 3497612 B2 | 2/2004 |
| JP | 3834602 B2 | 10/2006 |
| JP | 4152075 B2 | 9/2008 |
| JP | 4273965 B2 | 6/2009 |
| JP | 4982752 B2 | 7/2012 |

OTHER PUBLICATIONS

Luprasol® types (Technical Information Sep. 2010; 4 pages).*
Fischer et al. In vitro cytotoxicity testing of polycations: influence of polymer structure on cell viability and hemolysis, Biomaterials, 2003;24:1121-1131.*
Japanese Ministry of Health, Labour and Welfare, "Basic Principles of Biological Safety Evaluation Required for Application for Approval to Manufacture (Import) Medical Devices", *PFSB/ELD (Iyakushin) Notification* No. 0213001, Feb. 13, 2003, pp. 1-8.

* cited by examiner

*Primary Examiner* — Ernst V Arnold
(74) *Attorney, Agent, or Firm* — DLA Piper LLP (US)

(57) ABSTRACT

An antithrombogenic material includes a coating material containing: a polymer containing, as a constituent monomer, a compound selected from the group consisting of alkyleneimines, vinylamines, allylamines, lysine, protamine and diallyldimethylammonium chloride; and an anionic compound containing a sulfur atom and having anticoagulant activity; and a base material whose surface is coated with the coating material; wherein the polymer is covalently bound to the base material; and an abundance ratio of nitrogen atoms to an abundance of total atoms as measured by X-ray photoelectron spectroscopy (XPS) on a surface of the base material is 6.0 to 12.0 atomic percent.

11 Claims, No Drawings

ANTITHROMBOTIC MATERIAL

TECHNICAL FIELD

This disclosure relates to an antithrombogenic material.

BACKGROUND

Medical equipment and medical instruments that are brought into contact with blood (artificial kidneys, artificial lungs, artificial blood vessels, artificial valves, stents, stent-grafts, catheters, free-thrombus capture devices, angioscopes, sutures, blood circuits, tubes, cannulae, blood bags, syringes, and the like) are required to have high antithrombogenicity to prevent functional deterioration due to blood coagulation. In methods commonly used to impart antithrombogenicity to medical equipment and medical instruments, heparin or a heparin derivative as an anticoagulant is applied or chemically bound to a surface of a base material.

As methods of binding heparin or a heparin derivative to a surface of a base material, 1) methods in which the heparin or heparin derivative is covalently bound to a functional group introduced to the surface of the base material; and 2) methods in which the heparin or heparin derivative is bound by ionic bonding to a positively charged cationic compound introduced to the surface of the base material; are mainly known.

As methods of 1), a method in which aldehyde-modified heparin prepared by oxidation by nitrous acid treatment is covalently bound to the surface of the base material (JP 4152075 B), a method in which amino-modified heparin is bound to a cationic compound, polyethyleneimine (hereinafter referred to as "PEI"), to allow covalent bonding to the surface of the base material to which radicals are introduced (JP 3497612 B), and a method in which PEI introduced to the surface of the base material is covalently bound to heparin in the presence of a reducing agent (Japanese Translated PCT Patent Application Laid-open No. 10-513074), have been reported.

As methods of 2), methods in which, taking advantage of the fact that heparin and heparin derivatives are ionically negatively charged, heparin or a heparin derivative is bound by ionic bonding to a positively charged cationic compound have been reported (JP 60-041947 B, JP 60-047287 B, JP 4273965 B and JP 10-151192 A). Since, in antithrombogenic materials obtained by these methods, elution of the heparin or heparin derivative occurs with time, the strength of antithrombogenicity can be controlled by changing the amount of the heparin or heparin derivative bound and/or the elution rate thereof. Therefore, various combinations with positively charged cationic compounds have been studied.

For example, methods in which a surface of polyethylene terephthalate (hereinafter referred to as "PET") or polyamide as a base material is treated with polyamine, which is a cationic compound, by aminolysis or amide formation reaction, and heparin is bound thereto by ionic bonding, to obtain an antithrombogenic material (JP 60-041947 B and JP 60-047287 B), and methods in which an ionic complex is formed between an organic cation mixture such as a quaternary ammonium salt, or a quaternary phosphonium compound, and heparin or a heparin derivative, and the resulting ion complex is dissolved in an organic solvent, followed by applying the solution to a surface of a base material, thereby obtaining an antithrombogenic material (JP 4273965 B and JP 10-151192 A), have been reported. As other methods, a method in which a polymer containing a tertiary amino group is applied to a surface of a base material, and the amino group is then modified with a quaternary ammonium, followed by binding heparin thereto by ionic bonding, thereby obtaining an antithrombogenic material (JP 3341503 B), and methods in which PEI, which is a cationic compound, is introduced to a surface of a base material by ozone treatment or plasma treatment, and heparin is then bound thereto by ionic bonding, thereby obtaining an antithrombogenic material (JP 3497612 B and JP 3834602 B), have been reported.

A method in which a negatively charged, protein non-adsorptive substance such as heparin is bound to a surface of a base material to inhibit adsorption of cells to the surface has also been reported (JP 4982752 B).

However, in the methods disclosed in JP 4152075 B, JP 3497612 B and Japanese Translated PCT Patent Application Laid-open No. 10-513074, the degree of freedom of the heparin or heparin derivative decreases due to its covalent bonding, and it is therefore difficult to obtain the antithrombogenicity required.

JP 3497612 B, Japanese Translated PCT Patent Application Laid-open No. 10-513074, JP 60-041947 B and JP 60-047287 B describe methods in which a positively charged cationic compound such as polyamine is introduced to a surface of a base material, and heparin or a heparin derivative, which is an anionic compound having anticoagulant activity, is bound to the cationic compound by ionic bonding to achieve immobilization. However, there is no description on an appropriate amount of the heparin or heparin derivative to be introduced.

In the methods disclosed in JP 4273965 B and JP 10-151192 A, an ionic complex containing heparin and the like is dissolved in an organic solvent, and the resulting solution is applied to a base material. However, the organic solvent used needs to be a solvent in which the ionic complex is soluble, while the base material is insoluble. In the drying process after application, highly hydrophilic portions in the ionic complex avoid the organic solvent to cause aggregation. Since this leads to phase separation, the solution cannot be uniformly applied to the surface of the base material at present. Moreover, covalent bonding of an organic cation mixture such as a quaternary ammonium salt, or a low-molecular-weight compound such as a quaternary phosphonium compound, to the base material does not occur only by its application. Therefore, in use as an antithrombogenic material, elution easily occurs when it is bought into contact with a body fluid such as blood, and the elution rate of the heparin or heparin derivative cannot be controlled.

JP 3341503 B, JP 3497612 B and JP 3834602 B describe methods in which a surface of a base material is coated with a cationic polymer having an amino group, and heparin is then bound to the cationic polymer by ionic bonding. However, no study has been made on an appropriate amount of the polymer to be introduced to the surface of the base material. When the amount of the polymer for coating is too small, high antithrombogenicity cannot be obtained, while when the amount is too large, the structure on the surface of the base material may be embedded.

As described in JP 4982752 B, it is conventionally known that attachment of heparin or the like to the base material leads to a decrease in adhesiveness of cells to the surface of the base material. Thus, when an antithrombogenic material using heparin or the like is used for an artificial blood vessel, stent, stent-graft, or the like, thrombosis can be prevented, but biological incorporation of the material by adhesion/growth of endothelial cells and the like may be inhibited.

In view of this, it could be helpful to provide an antithrombogenic material that is highly safe with its low hemolytic toxicity, and capable of maintaining high antithrombogenicity for a long period.

It could also be helpful to provide an antithrombogenic material that does not decrease adhesiveness of cells to the surface of the base material while the antithrombogenicity is maintained.

SUMMARY

We thus provide:

(1) An antithrombogenic material comprising:
a coating material containing:
a polymer containing, as a constituent monomer, a compound selected from the group consisting of alkyleneimines, vinylamines, allylamines, lysine, protamine, and diallyldimethylammonium chloride; and
an anionic compound containing a sulfur atom and having anticoagulant activity; and
a base material whose surface is coated with the coating material;
wherein
the polymer is covalently bound to the base material; and
the abundance ratio of nitrogen atoms to the abundance of total atoms as measured by X-ray photoelectron spectroscopy (XPS) on the surface is 6.0 to 12.0 atomic percent.

(2) The antithrombogenic material according to (1), wherein the abundance ratio of sulfur atoms to the abundance of total atoms as measured by X-ray photoelectron spectroscopy (XPS) on the surface is 3.0 to 6.0 atomic percent.

(3) The antithrombogenic material according to (1) or (2), wherein the polymer has a quaternary ammonium group.

(4) The antithrombogenic material according to (3), wherein each carbon chain bound to the nitrogen atom in the quaternary ammonium group is constituted by an alkyl group, and the carbon number per alkyl group is 1 to 12.

(5) The antithrombogenic material according to any one of (1) to (4), wherein the coating material comprises:
an anionic polymer containing, as a constituent monomer, a compound selected from the group consisting of acrylic acid, methacrylic acid, α-glutamic acid, γ-glutamic acid, and aspartic acid; or
an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid.

(6) The antithrombogenic material according to any one of (1) to (4), wherein the anionic compound containing a sulfur atom and having anticoagulant activity is heparin or a heparin derivative.

(7) The antithrombogenic material according to any one of (1) to (6), wherein the weight average molecular weight of the polymer is 600 to 2,000,000.

(8) The antithrombogenic material according to (5), wherein the weight average molecular weight of the anionic polymer is 600 to 2,000,000.

(9) The antithrombogenic material according to any one of (1) to (8), wherein the abundance ratio of the n2 component as a split peak of nitrogen atoms to the total component of the N1s peak as measured by X-ray photoelectron spectroscopy (XPS) on the surface is 20 to 70 atomic percent.

(10) The antithrombogenic material according to any one of (1) to (9), wherein the abundance ratio of the c3 component as a split peak of carbon atoms to the total component of the C1s peak as measured by X-ray photoelectron spectroscopy (XPS) on the surface is not less than 2.0 atomic percent.

(11) The antithrombogenic material according to any one of (1) to (10), wherein the coating material has a mean thickness of 1 to 600 nm.

(12) The antithrombogenic material according to any one of (1) to (11), wherein the coating material is placed to a depth of 20 to 100 nm from an interface of the base material.

(13) The antithrombogenic material according to any one of (1) to (12), having cellular adhesiveness.

In addition, we also provide:

(14) An antithrombogenic material comprising:
a coating material containing:
a polymer containing, as a constituent monomer, a compound selected from the group consisting of alkyleneimines, vinylamines, allylamines, lysine, protamine, and diallyldimethylammonium chloride; and
heparin or a heparin derivative; and
a base material whose surface is coated with the coating material;
wherein
the polymer is covalently bound to the base material; and
the abundance ratio of nitrogen atoms to the abundance of total atoms as measured by X-ray photoelectron spectroscopy (XPS) on the surface is 7.0 to 12.0 atomic percent.

(15) An antithrombogenic material comprising:
a coating material containing:
a polymer containing, as a constituent monomer, a compound selected from the group consisting of alkyleneimines, vinylamines, allylamines, lysine, protamine, and diallyldimethylammonium chloride; and
an anionic compound containing a sulfur atom and having anticoagulant activity; and
a base material whose surface is coated with the coating material;
wherein
the polymer is covalently bound to the base material; and
the abundance ratio of sulfur atoms to the abundance of total atoms as measured by X-ray photoelectron spectroscopy (XPS) on the surface is 3.0 to 6.0 atomic percent.

(16) The antithrombogenic material according to (14) or (15), wherein the surface amount estimated based on anti-factor Xa activity after immersion in physiological saline for 30 minutes is not less than 30 mIU/cm$^2$.

(17) The antithrombogenic material according to any one of (14) to (16), wherein the total coating amount estimated based on anti-factor Xa activity is not more than 10,000 mIU/cm$^2$.

Since the antithrombogenic material can maintain the structure of the surface of the base material, suppress elution of components other than the anionic compound containing a sulfur atom and having anticoagulant activity through a polymer covalently bound to the base material, and exhibit anticoagulant activity for a long period, the antithrombogenic material can be preferably used for medical equipment and medical instruments requiring antithrombogenicity (artificial kidneys, artificial lungs, artificial blood vessels, artificial valves, stents, stent-grafts, catheters, free-thrombus capture devices, angioscopes, sutures, blood circuits, tubes, cannulae, blood bags, syringes and the like).

DETAILED DESCRIPTION

The antithrombogenic material comprises: a coating material containing a polymer containing, as a constituent monomer, a compound selected from the group consisting of alkyleneimines, vinylamines, allylamines, lysine, protamine, and diallyldimethylammonium chloride, and an anionic compound containing a sulfur atom and having anticoagulant activity; and a base material whose surface is coated with the coating material; wherein the polymer is covalently bound to the base material, and the abundance ratio of nitrogen atoms to the abundance of total atoms as measured by X-ray photoelectron spectroscopy (hereinafter referred to as "XPS") on the surface is 6.0 to 12.0 atomic percent.

The following terms are defined as described below unless otherwise specified.

The term "antithrombogenicity" means a property that prevents blood coagulation on a surface in contact with blood. For example, "antithrombogenicity" means a property that inhibits platelet aggregation, or blood coagulation which proceeds due to, for example, activation of blood coagulation factors represented by thrombin.

The term "antithrombogenic material" means a material having antithrombogenicity. The "antithrombogenic material" may, but does not necessarily need to be used as a material constituting medical equipment and medical instruments (artificial kidneys, artificial lungs, artificial blood vessels, artificial valves, stents, stent-grafts, catheters, free-thrombus capture devices, angioscopes, sutures, blood circuits, tubes, cannulae, blood bags, syringes and the like). The medical equipment and medical instruments are frequently brought into contact with blood and blood coagulation is likely to proceed on surfaces of the medical equipment and medical instruments. Therefore, antithrombogenic materials need to be used as materials for such medical equipment and medical instruments.

Among the materials constituting an antithrombogenic material, the "base material" means a substance constituting a surface to be coated with the coating material defined below. Preferred examples of the material of the base material include, but are not limited to, polyesters, expanded porous polytetrafluoroethylene (hereinafter referred to as "ePTFE"), polyurethane, polyetherurethane, polyamide, vinyl chloride, polycarbonate, polystyrene, polyethylene, polypropylene, polymethylpentene, and polymethyl methacrylate. Among these, polyesters are preferred as the base material of the antithrombogenic material because of their versatility, and polymers containing at least an ester as a constituent monomer are more preferred. Examples of the polymers include PET, polytrimethylene terephthalate, polybutylene terephthalate, polyethylene naphthalate, and polybutylene naphthalate. Among these, PET is more preferred as the base material of the antithrombogenic material because of its versatility.

The "coating material" means a material with which at least a part of the surface of the base material is coated, and the coating material contains: a polymer containing, as a constituent monomer, a compound selected from the group consisting of alkyleneimines, vinylamines, allylamines, lysine, protamine, and diallyldimethylammonium chloride; and an anionic compound containing a sulfur atom and having anticoagulant activity.

The polymer constituting the coating material is a polymer containing, as a constituent monomer, a compound selected from the group consisting of alkyleneimines, vinylamines, allylamines, lysine, protamine, and diallyldimethylammonium chloride. Since these constituent monomers have a cationic nitrogen atom, the polymer becomes cationic. On the other hand, the compound containing a sulfur atom and having anticoagulant activity is anionic, and can therefore bind to the polymer by ionic bonding. Examples of the anionic compound containing a sulfur atom and having anticoagulant activity include heparin and heparin derivatives, dextran sulfate, polyvinyl sulfonate, and polystyrene sulfonate. Heparin and heparin derivatives are more preferred. The heparin and heparin derivatives are not limited as long as blood coagulation reaction can be inhibited therewith, and examples of the heparin and heparin derivatives include heparin which is clinically generally and widely used, unfractionated heparin, and low-molecular-weight heparin, as well as heparins having high affinity to antithrombin III.

Since the polymer constituting the coating material has cationic properties, it may exhibit cytotoxicity. Therefore, elution of the polymer into a body fluid such as blood is not preferred. Thus, the polymer constituting the coating material is preferably covalently bound to the surface of the base material.

The covalent bonding herein means a chemical bond formed by sharing of an electron(s) between atoms. The covalent bond is a covalent bond between atoms such as carbon, nitrogen, oxygen, and/or sulfur present on the surfaces of the polymer and the base material constituting the coating material, and may be a single bond or multiple bond. Examples of the type of the covalent bond include, but are not limited to, an amine bond, azide bond, amide bond, and imine bond. Among these, from the viewpoint of ease of formation of the covalent bond, stability after bonding, and the like, an amide bond is more preferred. As a result of intensive study, we discovered that, when amide bonds are formed between the polymer constituting the coating material and the surface of the base material, the configuration of the polymer on the surface of the base material optimizes the state of ionic bonding to the anionic compound containing a sulfur atom and having anticoagulant activity, for example, heparin or a heparin derivative. Confirmation of the covalent bonds is possible by judgment of whether elution occurs by washing with a solvent that dissolves the polymer.

The polymer constituting the coating material may be either a homopolymer or a copolymer. When the polymer is a copolymer, the copolymer may be any of a random copolymer, block copolymer, graft copolymer, and alternating copolymer. The polymer constituting the coating material is more preferably a block copolymer since, in a block copolymer, stronger ionic bonding can be achieved by interaction between a block portion(s) having continuous repeat units containing nitrogen atoms, and the anionic compound containing a sulfur atom and having anticoagulant activity.

The homopolymer herein means a macromolecular compound obtained by polymerization of a single kind of constituent monomers. The copolymer herein means a macromolecular compound obtained by copolymerization of two or more kinds of monomers. The block copolymer means a copolymer having a molecular structure in which at least two kinds of polymers having different repeat units are covalently bound to each other to form a longer chain. The block means each of the "at least two kinds of polymers having different repeat units" constituting the block copolymer.

The structure of the polymer may be either linear or branched. The polymer is preferably branched since a branched polymer can form more stable ionic bonds at multiple positions with the anionic compound containing a sulfur atom and having anticoagulant activity.

The polymer has at least one functional group selected from primary to tertiary amino groups and a quaternary ammonium group. In particular, the polymer more preferably has a quaternary ammonium group rather than primary to tertiary amine groups since a quaternary ammonium group has stronger ionic interaction with the anionic compound containing a sulfur atom and having anticoagulant activity, and hence allows easier control of the elution rate of the anionic compound containing a sulfur atom and having anticoagulant activity.

The carbon numbers of the three alkyl groups constituting the quaternary ammonium group are not limited. However, when the carbon numbers are too large, hydrophobicity is high, and steric hindrance is enhanced so that the anionic compound containing a sulfur atom and having anticoagulant activity cannot effectively bind to the quaternary ammonium group by ionic bonding. Moreover, when the carbon number is too large, the polymer is more likely to show cytotoxicity so that the carbon number per alkyl group bond to the nitrogen atom constituting the quaternary ammonium group is preferably 1 to 12, more preferably 2 to 6. The carbon numbers of the three alkyl groups bound to the nitrogen atom constituting the quaternary ammonium group may be the same as or different from each other.

A polyalkyleneimine is preferably used as the polymer since the amount of the anionic compound containing a sulfur atom and having anticoagulant activity adsorbed thereto by ionic interaction is large. Examples of the polyalkyleneimine include PEI, polypropyleneimines, and polybutyleneimines, as well as alkoxylated polyalkyleneimines. Among these, PEI is more preferred.

Specific examples of the PEI include "LUPASOL" (registered trademark) (manufactured by BASF), and "EPOMIN" (registered trademark) (manufactured by Nippon Shokubai Co., Ltd.). The PEI may be a copolymer with one or more other monomers or a modified body as long as the desired effect is not deteriorated. The modified body herein means a polymer having the same monomer repeat units constituting the polymer, but has partially undergone, for example, radical decomposition or recombination due to the later-mentioned radiation irradiation.

The constituent monomer(s) used to form the copolymer other than alkyleneimines, vinylamines, allylamines, lysine, protamine, and diallyldimethylammonium chloride is/are not limited, and examples of the constituent monomer(s) include ethylene glycol, propylene glycol, vinylpyrrolidone, vinyl alcohol, vinylcaprolactam, vinyl acetate, styrene, methyl methacrylate, hydroxyethyl methacrylate, and siloxane. The content of the constituent monomer(s) used to form the copolymer other than alkyleneimines, vinylamines, allylamines, lysine, protamine, and diallyldimethylammonium chloride is preferably not more than 10% by weight since ionic bonding with the anionic compound containing a sulfur atom and having anticoagulant activity is weak when the content is too large.

When the weight average molecular weight of the polymer constituting the coating material is too small, and smaller than the molecular weight of the anionic compound containing a sulfur atom and having anticoagulant activity, stable ionic bonds cannot be formed on the surface of the base material so that the antithrombogenicity of interest is less likely to be obtained. On the other hand, when the weight average molecular weight of the polymer is too large, the anionic compound containing a sulfur atom and having anticoagulant activity is included in the inside of the polymer so that the anionic compound is not exposed on the outermost surface of the coating material. Thus, the weight average molecular weight of the polymer constituting the coating material is preferably 600 to 2,000,000, more preferably 1000 to 1,500,000, still more preferably 10,000 to 1,000,000. The weight average molecular weight of the polymer can be measured by, for example, gel permeation chromatography or the light scattering method.

The heparin or heparin derivative constituting the coating material may be either purified or not purified. The heparin or heparin derivative is not limited as long as blood coagulation reaction can be inhibited therewith, and examples of the heparin or heparin derivative include heparin which is clinically generally and widely used, unfractionated heparin, and low-molecular-weight heparin, as well as heparins having high affinity to antithrombin III. Specific examples of the heparin include "heparin sodium" (manufactured by Organon API Inc.).

We studied to maintain high antithrombogenic activity of the anionic compound containing a sulfur atom and having anticoagulant activity for a long period while the structure of the surface of the base material is maintained and elution of components other than the anionic compound containing a sulfur atom and having anticoagulant activity is suppressed. As a result, we discovered that there is a preferred value of the abundance ratio of sulfur atoms to the abundance of total atoms as measured by XPS on the surface of the antithrombogenic material. The abundance ratio of atoms is expressed as "atomic percent", and the atomic percent means the ratio of a specific kind of atoms to the abundance of total atoms, which is taken as 100, in terms of the number of atoms.

That is, the abundance ratio of sulfur atoms to the abundance of total atoms as measured by XPS on the surface of the antithrombogenic material is preferably 3.0 to 6.0 atomic percent, more preferably 3.2 to 5.5 atomic percent, still more preferably 3.5 to 5.0 atomic percent. When the abundance ratio of sulfur atoms to the abundance of total atoms is less than 3.0 atomic percent, the coating amount of the anionic compound containing a sulfur atom and having anticoagulant activity is small and, therefore, the antithrombogenicity of interest cannot be obtained. On the other hand, we found that, when the abundance ratio of sulfur atoms to the abundance of total atoms is higher than 6.0 atomic percent, the coating amount of the anionic compound containing a sulfur atom and having anticoagulant activity is sufficient, and the antithrombogenicity of interest can therefore be obtained, but the amount of the polymer to be covalently bound to the surface of the base material to allow the ionic bonding needs to be large so that as elution proceeds, a large amount of exposed polymer exhibits hemolytic toxicity due to its cationic properties.

When the abundance ratio of sulfur atoms to the abundance of total atoms is not more than 6.0 atomic percent, the coating amount of the anionic compound containing a sulfur atom and having anticoagulant activity is appropriate so that adhesiveness of endothelial cells can be increased.

More specifically, the abundance ratio of sulfur atoms to the abundance of total atoms on the surface of the antithrombogenic material can be determined by XPS.

Measurement Conditions

Apparatus: ESCALAB 220iXL (manufactured by VG Scientific)

Excitation X-ray: monochromatic A1K α1, 2 ray (1486.6 eV)

X-ray diameter: 1 mm

X-electron escape angle: 90° (the angle of the detector with respect to the surface of the antithrombogenic material)

The surface of the antithrombogenic material herein means the portion from the measurement surface to a depth of 10 nm as detected under the measurement conditions in XPS wherein the X-electron escape angle, that is, the angle of the detector with respect to the surface of the antithrombogenic material, is 90°. The base material may or may not contain sulfur atoms. The base material may or may not contain nitrogen atoms.

By radiating X-ray to the surface of the antithrombogenic material, and measuring the energy of photoelectrons generated therefrom, the binding energy values of bound electrons in the substance can be determined. From the binding energy values, information on the atoms on the surface of the antithrombogenic material can be obtained and, from the energy shift of the peak at each binding energy value, information on the valence and the binding state can be obtained. In addition, by using the peak area ratio of each peak, quantification, that is, calculation of the abundance ratios of each kind of atoms, valence, and binding state, is possible.

More specifically, the S2p peak, that indicates the presence of sulfur atoms, appears near a binding energy value of 161 eV to 170 eV. We discovered that the area ratio of the S2p peak in the whole peak is preferably 3.0 to 6.0 atomic percent. In the calculation of the abundance ratio of sulfur atoms to the abundance of total atoms, the obtained value is rounded to one decimal place.

Similarly, by XPS measurement, we discovered that there are optimal values of the abundance ratio of nitrogen atoms to the abundance of total atoms as measured by XPS on the surface of the antithrombogenic material. That is, the abundance ratio of nitrogen atoms to the abundance of total atoms as measured by XPS on the surface of the antithrombogenic material is preferably 6.0 to 12.0 atomic percent, more preferably 7.0 to 12.0 atomic percent, still more preferably 7.5 to 11.0 atomic percent, still more preferably 8.0 to 10.0 atomic percent, from the viewpoint of increasing the antithrombogenicity. When the abundance ratio of nitrogen atoms to the abundance of total atoms is less than 6.0 atomic percent, the amount of the polymer covalently bound to the surface of the base material is small so that the structure of the surface of the base material can be maintained. However, since the coating amount of the anionic compound containing a sulfur atom and having anticoagulant activity such as heparin or a heparin derivative that binds to the surface through the polymer is small in such cases, the antithrombogenicity of interest cannot be obtained. On the other hand, we found that when the abundance ratio of nitrogen atoms to the abundance of total atoms is higher than 12.0 atomic percent, the amount of the polymer covalently bound to the surface of the base material is large so that the coating amount of the anionic compound containing a sulfur atom and having anticoagulant activity bound through the polymer by ionic bonding is sufficient. However, we also found that, as elution of the compound containing a sulfur atom and having anticoagulant activity proceeds, a large amount of exposed polymer exhibits hemolytic toxicity due to its cationic properties.

When the abundance ratio of nitrogen atoms to the abundance of total atoms is not more than 12.0 atomic percent, the coating amount of the anionic compound containing a sulfur atom and having anticoagulant activity is appropriate so that adhesiveness of endothelial cells can be increased. To achieve both antithrombogenicity and cellular adhesiveness, the abundance ratio of nitrogen atoms to the abundance of total atoms as measured by XPS on the surface of the antithrombogenic material is preferably 6.0 to 12.0 atomic percent, more preferably 6.0 to 9.5 atomic percent, still more preferably 8.0 to 9.5 atomic percent.

More specifically, the N1s peak, which indicates the presence of nitrogen atoms, appears near a binding energy value of 396 eV to 403 eV. We discovered that the area ratio of the N1s peak in the whole peak is preferably 6.0 to 12.0 atomic percent. The N1s peak can be split into the n1 component (near 399 eV), which is attributed to carbon-nitrogen (hereinafter referred to as "C—N") bonds; and the n2 component (near 401 to 402 eV), which is attributed to ammonium salt, C—N(structure different from n1), and/or nitrogen oxide (hereinafter referred to as "NO"). The abundance ratio of each split peak component can be calculated according to Equation 1 below. In this calculation, the abundance ratio of nitrogen atoms and the abundance ratio of each split peak component to the abundance of total atoms are rounded to one decimal place.

$$\text{Split}_{ratio} = N1s_{ratio} \times (\text{Split}_{percent}/100) \quad (1)$$

$\text{Split}_{ratio}$: Abundance ratio of each split peak component (%)

$N1s_{ratio}$: Abundance ratio of nitrogen atoms to the abundance of total atoms (%)

$\text{Split}_{percent}$: Ratio of each split peak component in the N1s peak (%)

The n2 component, which is attributed to NO, obtained by splitting the N1s peak indicates the presence of quaternary ammonium groups. We discovered that the ratio of the n2 component in the total component of the N1s peak, that is $\text{Split}_{percent}$ (n2), is preferably 20 to 70 atomic percent, more preferably 25 to 65 atomic percent, still more preferably 30 to 60 atomic percent. When $\text{Split}_{percent}$ (n2) is less than 20 atomic percent, the abundance of quaternary ammonium groups is low. Therefore, the ionic interaction with the anionic compound containing a sulfur atom and having anticoagulant activity is weak, and the antithrombogenicity of interest is less likely to be obtained because of high elution rate. On the other hand, when $\text{Split}_{percent}$ (n2) is higher than 70 atomic percent, the ionic interaction with the anionic compound containing a sulfur atom and having anticoagulant activity is too strong. In such cases, because of a decrease in the degree of freedom due to formation of an ionic complex, it is impossible to maintain a high anticoagulant activity for a long period, and the elution rate tends be low. Because of the above reasons, the abundance ratio of the n2 component, that is, $\text{Split}_{ratio}$ (n2), which is calculated according to Equation 1, is preferably 1.4 to 8.4 atomic percent, more preferably 1.8 to 7.2 atomic percent, still more preferably 2.4 to 6.0 atomic percent.

The C1s peak, which indicates the abundance of carbon atoms, appears near a binding energy value of 282 to 292 eV. The C1s peak can be mainly split into the c1 component (near 285 eV), which is attributed to carbon-hydrogen (hereinafter referred to as "CHx") bonds suggesting the presence of a saturated hydrocarbon(s) and/or the like, to carbon-carbon (hereinafter referred to as "C—C") bonds, and/or to carbon=carbon (hereinafter referred to as "C=C") bonds; the c2 component (near 286 eV), which is attributed to carbon-oxygen (hereinafter referred to as "C—O") bonds suggesting the presence of an ether(s) and/or hydroxyl groups, and/or to carbon-nitrogen (hereinafter referred to as "C—N") bonds; the c3 component (near 287 to 288 eV), which is attributed to carbon=oxygen (hereinafter referred to as "C=O") bonds suggesting the presence of carbonyl groups; the c4 component (near 288 to 289 eV), which is attributed to oxygen=carbon-oxygen (hereinafter referred to as "O=C—O") bonds suggesting the presence of ester groups and/or carboxyl groups; and the c5 component (near 290 to 292 eV), which is attributed to π-π*satellite peak (hereinafter referred to as "π-π") bonds suggesting the presence of a conjugated system(s) such as benzene rings.

The abundance ratio of each split peak component can be calculated according to Equation 2 below. In this calculation, the abundance ratio of carbon atoms and the abundance ratio of each split peak component to the abundance of total atoms are rounded to one decimal place.

$$\text{Split}_{ratio} = C1s_{ratio} \times (\text{Split}_{percent}/100) \qquad (2)$$

Split$_{ratio}$: Abundance ratio of each split peak component (%)

C1s$_{ratio}$: Abundance ratio of carbon atoms to the abundance of total atoms (%)

Split$_{percent}$: Ratio of each split peak component in the C1s peak (%)

The c3 component, which is attributed to C=O bonds, obtained by splitting the C1s peak indicates the presence of amide groups. We discovered that the ratio of the c3 component in the total component of the C1s peak, that is, the abundance ratio of amide groups as measured by XPS on the surface of the antithrombogenic material, is preferably not less than 2.0 atomic percent, more preferably not less than 3.0 atomic percent. When the abundance ratio of the amide groups is less than 2.0 atomic percent, the number of covalent bonds due to amide bonds between the polymer constituting the coating material and the surface of the base material is small, and therefore the coating amount of the coating material is small. Moreover, the configuration of the polymer on the surface of the base material adversely affects the state of ionic bonding with the anionic compound containing a sulfur atom and having anticoagulant activity. Thus, the antithrombogenicity of interest is less likely to be obtained.

The antithrombogenic material can be favorably used for medical equipment and medical instruments (artificial kidneys, artificial lungs, artificial blood vessels, artificial valves, stents, stent-grafts, catheters, free-thrombus capture devices, angioscopes, sutures, blood circuits, tubes, cannulae, blood bags, syringes, and the like). The antithrombogenic material is especially preferably used as a material for free-thrombus capture devices and artificial blood vessels.

When the antithrombogenic material is used for a free-thrombus capture device, it is preferred to use the antithrombogenic material for all constituents of the free-thrombus capture device. Since the porous material, which is the constituent for capturing free thrombi, requires highest antithrombogenicity, at least the porous material as the base material may be coated with the coating material. Examples of the porous material as the base material include, but are not limited to, porous membranes and meshes. Meshes are preferred since they have better uniformity of pores or apertures. Preferred examples of the material of the porous material include, but are not limited to, metals such as nickel-titanium alloy, and polyurethanes and polyesters. PET, which is a polyester, is more preferably used.

From the viewpoint of increasing the accuracy of capturing free thrombi, when the mesh as the material is PET, the single fiber diameter of the fibers constituting the mesh is preferably 10 µm to 50 µm, more preferably 20 µm to 40 µm. The mesh aperture is preferably 10 µm to 200 µm, more preferably 50 µm to 150 µm.

When the antithrombogenic material is used for an artificial blood vessel, it is preferred to use the antithrombogenic material for all constituents of the artificial blood vessel. Since the inner surface of the artificial blood vessel is in contact with blood, and therefore requires highest antithrombogenicity, at least the inner surface of the artificial blood vessel as the base material may be coated with the coating material. Preferred examples of the material constituting the inner surface of the artificial blood vessel as the base material include, but are not limited to, fabric structures composed of warp and weft yarns constituted by monofilaments or multifilaments. Preferred examples of the material of the base material include, but are not limited to, nylons and polyesters, and ePTFE. PET, which is a polyester, is more preferably used.

From the viewpoint of achieving favorable flexibility of the artificial blood vessel, when the mesh as the material is PET, monofilaments and multifilaments having a single fiber diameter of not more than 15 µm are preferred; monofilaments and multifilaments having a single fiber diameter of not more than 10 µm are more preferred; and monofilaments and multifilaments having a single fiber diameter of not more than 5 µm are still more preferred.

In a conventional antithrombogenic material, coating of the mesh as the base material with a coating material may cause destruction of the microstructure of the mesh, apertures, leading to a decrease in the accuracy of capturing thrombi. Moreover, destruction of the microstructure of the inner surface of the artificial blood vessel, that is, the fabric structure composed of warp and weft yarns, may affect blood blow and/or the like to promote thrombus formation. However, for example, in the antithrombogenic material, when coating with the polymer is carried out such that the abundance ratio of nitrogen atoms to the abundance of total atoms as measured by XPS is not more than 12.0 atomic percent, and coating with the anionic compound containing a sulfur atom and having anticoagulant activity is carried out such that the abundance ratio of sulfur atoms to the abundance of total atoms as measured by XPS is not more than 6.0 atomic percent on the surface of the antithrombogenic material, the thickness of the coating material is 1 to 600 nm so that high antithrombogenicity can be maintained for a long period without destroying the microstructure of apertures of the mesh used for a free-thrombus capture device, or the microstructure of the fabric structure used for the inner surface of an artificial blood vessel.

When the mean thickness of the coating material with which the base material is coated is too large, the microstructure of the surface of the base material may be destroyed. Therefore, the mean thickness is preferably 1 to 600 nm, more preferably 1 to 200 nm, still more preferably 1 to 100 nm. The mean thickness herein means the thickness in which atoms derived from the coating material can be observed using the later-mentioned scanning transmission electron microscope (hereinafter referred to as "STEM"). The mean thickness is expressed as a mean of the values obtained at at least three positions.

Methods of producing the antithrombogenic material are described below. For example, in preparation of fibers constituting the mesh as the base material of a free-thrombus capture device, or in preparation of fibers constituting the fabric structure as the base material of an artificial blood vessel, coating with the coating material may be carried out by adding the base material of interest to a solution which contains a polymer containing, as a constituent monomer, a compound selected from the group consisting of alkyleneimines, vinylamines, allylamines, lysine, protamine, and diallyldimethylammonium chloride, and the anionic compound containing a sulfur atom and having anticoagulant activity. Alternatively, the surface of the base material may be coated with the coating material after entirely or partially reacting the polymer with the anionic compound containing a sulfur atom and having anticoagulant activity.

In particular, from the viewpoint of efficiently allowing the surface of the base material to exhibit antithrombogenicity, a method in which the polymer containing, as a constituent monomer, a compound selected from the group consisting of alkyleneimines, vinylamines, allylamines, lysine, protamine, and diallyldimethylammonium chloride, is covalently bound to the surface of the base material in a first coating step, and then the anionic compound containing a sulfur atom and having anticoagulant activity is bound to the polymer by ionic bonding in a second coating step, is more preferred.

When the polymer contains a primary to tertiary amino group(s), a step of modifying the polymer with quaternary ammonium may be included after the first coating step to increase ionic interaction with the anionic compound containing a sulfur atom and having anticoagulant activity, and enable easy control of the elution rate of the anionic compound containing a sulfur atom and having anticoagulant activity.

The following is a production method where the method in which the polymer containing, as a constituent monomer, a compound selected from the group consisting of alkyleneimines, vinylamines, allylamines, lysine, protamine, and diallyldimethylammonium chloride, is covalently bound to the surface of the base material in a first coating step, and then the anionic compound containing a sulfur atom and having anticoagulant activity is bound to the polymer by ionic bonding in a second coating step, is used.

The method of covalent bonding of the polymer to the surface of the base material is not limited. When the base material has a functional group(s) (for example, hydroxyl, thiol, amino, carboxyl, aldehyde, isocyanate, and/or thioisocyanate), the polymer may be covalently bound thereto by chemical reaction. For example, when the surface of the base material has a carboxyl group and/or the like, a polymer having a hydroxyl group, thiol group, amino group, and/or the like may be covalently bound to the surface of the base material. Examples of the method of covalent bonding include a method in which a compound having a hydroxyl group, thiol group, amino group, and/or the like is covalently bound to the polymer, and the resulting polymer is covalently bound to the surface of the base material having a carboxyl group and/or the like.

When the base material does not have a functional group, examples of the method of covalent bonding include a method in which the surface of the base material is treated with plasma, corona, or the like, followed by covalent bonding of the polymer thereto, and a method in which radiation irradiation is performed to cause generation of radicals on the surface of the base material and the polymer, and covalent bonding between the surface of the base material and the polymer is achieved by recombination reaction of the radicals. As the radiation, γ-ray or electron beam is mainly employed. When γ-ray is employed, the amount of the γ-ray source is preferably 2,500,000 to 10,000,000 Ci, more preferably 3,000,000 to 7,500,000 Ci. When electron beam is employed, the accelerating voltage of the electron beam is preferably not less than 5 MeV, more preferably not less than 10 MeV. The radiation dose is preferably 1 to 50 kGy, more preferably 5 to 35 kGy. The irradiation temperature is preferably 10 to 60° C., more preferably 20 to 50° C.

In the method in which radiation irradiation is carried out for covalent bonding, an antioxidant may be used to control the amount of radicals generated. The antioxidant herein means a molecule that tends to give electrons to other molecules. Examples of the antioxidant to be used include, but are not limited to, water-soluble vitamins; polyphenols; alcohols such as methanol, ethanol, propanol, ethylene glycol, propylene glycol, and glycerin; sugars such as glucose, galactose, mannose, and trehalose; inorganic salts such as sodium hydrosulfite, sodium pyrosulfite, and sodium dithionate; uric acid; cysteine; glutathione; and buffers such as bis(2-hydroxyethyl)iminotris(hydroxymethyl)methane (hereinafter referred to as "Bis-Tris"). From the viewpoint of ease of handling, residual performance, and the like, methanol, ethanol, propylene glycol, and Bis-Tris are preferred. Propylene glycol and Bis-Tris are more preferred. These antioxidants may be used individually, or may be used as a mixture of two or more of these. The antioxidant is preferably added to an aqueous solution.

From the viewpoint of maintaining high antithrombogenicity for a longer period, a first additional step in which one or both of an anionic polymer comprising, as a constituent monomer, a compound selected from the group consisting of acrylic acid, methacrylic acid, α-glutamic acid, γ-glutamic acid, and aspartic acid; and at least one anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid;

is/are covalently bound to the surface of the polymer is preferably carried out after the first coating step. More preferably, after the first additional step of covalently binding the anionic polymer and/or anionic compound to the surface of the polymer, a second additional step in which a cationic polymer containing, as a constituent monomer, a compound selected from the group consisting of alkyleneimines, vinylamines, allylamines, lysine, protamine, and diallyldimethylammonium is covalently bound to the anionic polymer and/or anionic compound is carried out, followed by performing the second coating step in which an anionic compound containing a sulfur atom and having anticoagulant activity such as heparin or a heparin derivative is covalently bound to the cationic polymer. If necessary, a third and fourth additional steps may be carried out using an anionic polymer or anionic compound, and a cationic polymer.

The anionic polymer is preferably, but does not necessarily need to be, a polyacrylic acid (hereinafter referred to as "PAA"), polymethacrylic acid, poly(α-glutamic acid), poly (γ-glutamic acid), or polyaspartic acid since, when the weight ratio of anionic functional groups is high, a larger coating amount can be achieved by covalent bonding with the base material and the coating material. The anionic polymer is more preferably PAA.

Specific examples of the PAA include "polyacrylic acid" (manufactured by Wako Pure Chemical Industries, Ltd.). The PAA may be a copolymer with one or more other monomers or a modified body as long as the desired effect is not deteriorated.

The anionic polymer may, but does not necessarily need to, form a copolymer with one or more constituent monomers other than those described above. Examples of such monomers include ethylene glycol, propylene glycol, vinylpyrrolidone, vinyl alcohol, vinylcaprolactam, vinyl acetate, styrene, methyl methacrylate, hydroxyethyl methacrylate, and siloxane. The content of the constituent monomer(s) forming the copolymer with the anionic polymer is preferably not more than 10% by weight since the amount of coating formed by covalent bonding with the base material and the coating material is small when the content is too large.

When the weight average molecular weight of the anionic polymer is too small, the amount of coating formed by covalent bonding with the base material and the coating material is small so that high antithrombogenicity is less likely to be obtained. On the other hand, when the weight average molecular weight of the anionic polymer is too large, the coating material is included in the inside of the polymer. Thus, the weight average molecular weight of the anionic polymer is preferably 600 to 2,000,000, more preferably 10,000 to 1,000,000.

The anionic compound is preferably, but does not necessarily need to be, oxalic acid, malonic acid, succinic acid, fumaric acid, glutaric acid, adipic acid, pimelic acid, suberic acid, azelaic acid, sebacic acid, malic acid, tartaric acid, or citric acid since, when the weight ratio of anionic functional groups is high, a larger coating amount can be achieved by covalent bonding with the base material and the coating material. Succinic acid is more preferred.

When a polyester is used as the material of the base material, the polymer may be brought into contact therewith under heat to allow covalent bonding by aminolysis reaction, although the method of covalent bonding is not limited thereto. Alternatively, ester bonds on the surface of the base material may be hydrolyzed by acid or alkali treatment, and carboxyl groups generated on the surface of the base material may be covalently bound to amino groups in the polymer by condensation reaction. In these methods, the reaction may be carried out by bringing the polymer into contact with the surface of the base material, or by bringing a solution of the coating material in a solvent into contact with the surface of the base material. Preferred examples of the solvent include water and alcohols. From the viewpoint of ease of handling, residual performance, and the like, water is especially preferred. Alternatively, the monomers constituting the polymer may be polymerized in a state where the monomers are in contact with the surface of the base material, and the reaction may then be carried out to achieve covalent bonding.

Examples of the means for the heating include, but are not limited to, electric heating, microwave heating, and far-infrared heating. When the polymer is to be covalently bound to a polyester-based base material by aminolysis reaction, the aminolysis reaction of the polymer with the polyester-based base material is less likely to proceed at a low heating temperature. The heating temperature is therefore preferably not less than a temperature near the glass transition temperature. On the other hand, when the heating temperature is too high, the aminolysis reaction sufficiently proceeds, but the skeletal structure of the polyester-based base material is destroyed. The heating temperature is therefore preferably not more than the melting point.

We found that a step of hydrolyzing and oxidizing ester bonds on the surface of the base material before the first coating step is important. More specifically, a method in which treatment is carried out using an acid or an alkali, as well as an oxidizing agent, is preferably used. We found that the surface of the base material cannot be coated with a sufficient amount of the polymer by a method in which treatment is carried out with only an acid or an alkali. This is because, for example, in the method in which treatment is carried out using only an acid or an alkali, hydroxyl groups and carboxyl groups generated by hydrolysis of the ester bonds coexist, resulting in inefficient progress of the condensation reaction with amino groups in the polymer. Moreover, the presence of hydroxyl groups is not preferred since they are likely to activate complement when they are in contact with blood. That is, from the viewpoint of increasing antithrombogenicity by increasing the coating amount of the polymer without activating complement, the method in which treatment is carried out using an acid or an alkali, as well as an oxidizing agent, is especially preferably used.

In terms of the combination in the step of hydrolyzing and oxidizing ester bonds on the surface of the base material using an acid or an alkali, as well as an oxidizing agent, we discovered that a method in which treatment is carried out using an acid and an oxidizing agent is most preferred. The treatment using an acid and an oxidizing agent may be carried out after treating the surface of the base material using an alkali.

Examples of the type of the acid used include, but are not limited to, inorganic acids such as hydrochloric acid, hydrobromic acid, hydroiodic acid, hypochlorous acid, chlorous acid, perchloric acid, sulfuric acid, fluorosulfonic acid, nitric acid, phosphoric acid, hexafluoroantimonic acid, tetrafluoroboric acid, chromic acid, and boric acid; sulfonic acids such as methanesulfonic acid, ethanesulfonic acid, benzenesulfonic acid, p-toluenesulfonic acid, trifluoromethanesulfonic acid, and sodium polystyrene sulfonate; carboxylic acids such as acetic acid, citric acid, formic acid, gluconic acid, lactic acid, oxalic acid, and tartaric acid; vinyl carboxylic acids such as ascorbic acid and Meldrum's acid; and nucleic acids such as deoxyribonucleic acid and ribonucleic acid. Among these, hydrochloric acid, sulfuric acid and the like are more preferred from the viewpoint of, for example, ease of handling.

Examples of the type of the base used include, but are not limited to, hydroxides of alkali metals such as lithium hydroxide, sodium hydroxide, potassium hydroxide, rubidium hydroxide, and cesium hydroxide; hydroxides of tetraalkylammonium such as tetramethylammonium hydroxide and tetraethylammonium hydroxide; hydroxides of alkaline earth metals such as calcium hydroxide, strontium hydroxide, barium hydroxide, europium hydroxide, and thallium hydroxide; guanidine compounds; hydroxides of ammine complexes such as diammine silver (I) hydroxide and tetraammine copper (II) hydroxide; trimethylsulfonium hydroxide; and diphenyliodonium hydroxide. Among these, lithium hydroxide, sodium hydroxide, potassium hydroxide and the like are more preferred from the viewpoint of, for example, ease of handling.

Examples of the type of the oxidizing agent used include, but are not limited to, potassium nitrate; hypochlorous acid; chlorous acid; perchloric acid; halogens such as fluorine, chlorine, bromine, and iodine; permanganates such as potassium permanganate, sodium permanganate trihydrate, ammonium permanganate, silver permanganate, zinc permanganate hexahydrate, magnesium permanganate, calcium permanganate, and barium permanganate; ceric ammonium nitrate; chromic acid; dichromic acid; peroxides such as hydrogen peroxide solution; Tollens' reagent; and sulfur dioxide. Among these, permanganates are more preferred from the viewpoint of, for example, their strength as oxidizing agents and favorable prevention of deterioration of the antithrombogenic material.

Examples of the method of covalently binding the polymer to the surface of the polyester-based base material include a method in which condensation reaction is carried out using a dehydration-condensation agent or the like.

Examples of the type of the dehydration-condensation agent used include, but are not limited to, carbodiimide compounds such as N,N'-dicyclohexyl carbodiimide, N,N'-diisopropyl-carbodiimide, 1-ether-3-(3-dimethylaminopropyl)carbodiimide, 1-ether-3-(3-dimethylaminopropyl)carbodiimide hydrochloride (hereinafter referred to as "EDC"), 1,3-bis(2,2-dimethyl-1,3-dioxolan-4-ylmethyl)carbodiimide, N-{3-(dimethylamino)propyl-}-N'-ethylcarbodiimide, N-{3-(dimethylamino)propyl-}-N'-ethylcarbodiimide methiodide, N-tert-butyl-N'-ethylcarbodiimide, N-cyclohexyl-N'-(2-morpholinoethyl)carbodiimide, meso-p-toluenesulfonate, N,N'-di-tert-butylcarbodiimide, and N,N'-di-p-tricarbodiimide; and triazine compounds such as 4-(4,6-dimethoxy-1,3,5-triazin-2-yl)-4-methylmorpholinium chloride n-hydrate (hereinafter referred to as "DMT-MM").

The dehydration-condensation agent may be used together with a dehydration-condensation promoter. Examples of the dehydration-condensation promoter used include, but are not limited to, pyridine, 4-dimethylaminopyridine (hereinafter referred to as "DMAP"), triethylamine, isopropylamine, 1-hydroxybenzotriazole, and N-hydroxysuccinimide.

The polymer, dehydration-condensation agent, and dehydration-condensation promoter may be prepared as a mixed aqueous solution to be used for the reaction, or may be sequentially added to perform the reaction.

When ePTFE is used as a material of the base material, a method in which the surface of the base material is functionalized using plasma or corona may be used, although the method is not limited thereto. Alternatively, a method in which a fluorocarbon-resin surface treatment agent or the like is used for extraction of fluorine atoms present on the surface of the base material, and hydroxyl groups, carboxyl groups, carbonyl groups, and/or the like are formed by reaction with oxygen, hydrogen, water vapor and/or the like in the air, may be used.

In the same manner as in the polyester-based base material described above, a first coating step of covalently binding the polymer to the surface of the ePTFE base material may be carried out.

When the polymer contains a primary to tertiary amino group(s), a step of modifying the polymer with quaternary ammonium may be included to increase ionic interaction with the anionic compound containing a sulfur atom and having anticoagulant activity, and to enable easy control of the elution rate of the anionic compound containing a sulfur atom and having anticoagulant activity.

In terms of the method of modification of the polymer with quaternary ammonium, the polymer may be modified with quaternary ammonium before covalent bonding of the polymer to the surface of the base material, or the polymer may be modified with quaternary ammonium after covalent bonding of the polymer to the surface of the base material. From the viewpoint of increasing the ionic interaction between the polymer and the anionic compound containing a sulfur atom and having anticoagulant activity, quaternary ammonium groups contained in the polymer are preferably present on the outermost surface of the coating material. It is therefore preferred to modify the polymer with quaternary ammonium after covalent bonding of the polymer to the surface of the base material. More specifically, after covalently binding the polymer to the surface of the base material, an alkyl halide compound such as ether chloride or ethyl bromide, or a glycidyl-containing quaternary ammonium salt, may be directly brought into contact with the polymer, or may be brought into contact with the polymer after dissolving it in an aqueous solution or an organic solvent.

The second coating step of binding the anionic compound containing a sulfur atom and having anticoagulant activity to the polymer by ionic bonding is not limited, and a method in which the compound in a state of an aqueous solution is brought into contact with the polymer is preferred.

The anti-factor Xa activity on the surface of the antithrombogenic material was measured. The anti-factor Xa activity herein is an index indicating the degree of inhibition of the activity of factor Xa, which promotes conversion of prothrombin to thrombin. For example, when the anionic compound containing a sulfur atom and having anticoagulant activity in the antithrombogenic material is heparin or a heparin derivative, its surface amount can be known based on the unit of anti-factor Xa activity. For the measurement, "TESTZYM (registered trademark) Heparin S" (manufactured by Sekisui Medical Co., Ltd.) was used. When the anti-factor Xa activity is too low, the surface amount of the heparin or heparin derivative in the antithrombogenic material is small, and the antithrombogenicity of interest is less likely to be obtained. On the other hand, when the anti-factor Xa activity is too high, the surface amount of the heparin or heparin derivative is sufficient to achieve the antithrombogenicity of interest, but an increase in the thickness of the coating material may lead to difficulty in maintenance of the microstructure of the surface of the base material. That is, the anti-factor Xa activity is preferably 25 mIU/cm$^2$, more preferably 30 mIU/cm$^2$, still more preferably 50 mIU/cm$^2$. The surface amount estimated based on the anti-factor Xa activity herein means a value measured after 30 minutes of immersion in physiological saline.

The antithrombogenic material is characterized in that, irrespective of the fact that the total coating amount of the heparin or heparin derivative with which the surface of the base material is coated as estimated based on the anti-factor Xa activity is small, the initial surface amount of the heparin or heparin derivative after the 30 minutes of immersion in physiological saline is high. The total coating amount herein means the sum of the total amount of the heparin or heparin derivative eluted and the surface amount of the heparin or heparin derivative remaining on the surface of the antithrombogenic material as estimated based on the anti-factor Xa activity. When the total coating amount is too large, the microstructure of the surface of the base material is destroyed, while when the total coating amount is too small, the antithrombogenicity of interest is less likely to be obtained. That is, preferably, the total coating amount as estimated based on the anti-factor Xa activity on the surface of the antithrombogenic material is not more than 10,000 mIU/cm$^2$, and the initial surface amount after 30 minutes of immersion in physiological saline is not less than 25 mIU/cm$^2$. More preferably, the total coating amount is not more than 10,000 mIU/cm$^2$, and the initial surface amount after 30 minutes of immersion in physiological saline is not less than 30 mIU/cm$^2$. Still more preferably, the total coating amount is not more than 5000 mIU/cm$^2$, and the initial surface amount after 30 minutes of immersion in physiological saline is not less than 50 mIU/cm$^2$.

As an index indicating antithrombogenicity, the thrombus weight after contacting with human whole blood was quantified. Using the antithrombogenic material prepared by coating with the coating material and, as a positive control, the same type of base material which does not contain the coating material, tests were carried out in three replicates. Relative values of the thrombus weight were calculated according to Equation 3 and, when the mean of the relative values is not less than 10%, the amount of thrombi attached to the antithrombogenic material is small, which is preferred.

$$\text{Relative value of thrombus weight (\%)} = (Bt/Bp) \times 100 \qquad (3)$$

Bt: Thrombus weight of the sample
Bp: Thrombus weight of the positive control

Elution of the anionic compound containing a sulfur atom and having anticoagulant activity proceeds as the antithrombogenic material is continuously used. In this process, the exposed polymer might exhibit hemolytic toxicity because of its cationic properties. As an index indicating the hemolytic toxicity, the hemolysis rate calculated according to Equation 4 was used. Hemolytic toxicity is ranked into different grades based on the value of the hemolysis rate as shown in Table 1, according to the hemolytic toxicity test described in a guideline published by Ministry of Health, Labour and Welfare, "Basic Principles of Biological Safety Evaluation Required for Application for Approval to Market Medical Devices". The hemolytic toxicity is preferably ranked into the "nonhemolytic" or "mildly hemolytic" grade, more preferably ranked into the "nonhemolytic" grade.

$$\text{Hemolysis rate (\%)} = [(At-An)/(Ap-An)] \times 100 \quad (4)$$

At: Absorbance of the sample
An: Absorbance of the negative control
Ap: Absorbance of the positive control

TABLE 1

| Hemolysis rate (%) | Grade |
|---|---|
| Hemolysis rate < 2 | Nonhemolytic |
| 2 < Hemolysis rate < 10 | Mildly hemolytic |
| 10 < Hemolysis rate < 20 | Moderately hemolytic |
| 20 < Hemolysis rate < 40 | Strongly hemolytic |
| 40 < Hemolysis rate | Very strongly hemolytic |

The antithrombogenic material is further characterized in that the coating material constituted by the polymer, anionic compound containing a sulfur atom and having anticoagulant activity and the like is present not from the interface of the base material, but is also present in the depth direction from the interface of the base material, unlike known antithrombogenic materials.

More specifically, whether or not the coating material is present in the depth direction from the interface of the base material can be confirmed by combination of, for example, a STEM and XPS. A STEM has detectors such as an energy dispersive X-ray spectrometer (hereinafter referred to as "EDX") and an electron energy-loss spectrometer (hereinafter referred to as "EELS"). Measurement conditions for the STEM are as follows.

Measurement Conditions
 Apparatus: field emission transmission electron microscope JEM-2100F (manufactured by JEOL Ltd.)
 EELS detector: GIF Tridiem (manufactured by GATAN, Inc.)
 EDX detector: JED-2300T (manufactured by JEOL Ltd.)
 Image acquisition: Digital Micrograph (manufactured by GATAN, Inc.)
 Sample preparation: ultrathin sectioning (suspension using a copper microgrid; use of an acrylic resin as an embedding resin)
 Acceleration voltage: 200 kV
 Beam diameter: 0.7-nm diameter
 Energy resolution: about 1.0 eV FWHM The surface of the antithrombogenic material herein means the portion from the measurement surface to a depth of 10 nm as measured by XPS, and the interface of the antithrombogenic material herein means the border with the acrylic resin in which the antithrombogenic material is embedded during the sample preparation before the measurement using the STEM.

Whether or not the coating material is present in the depth direction from the interface of the base material can be confirmed by, for example, measurement using the STEM. The presence of the coating material can be confirmed by carrying out observation of atoms derived from the coating material which is the polymer and the anionic compound containing a sulfur atom and having anticoagulant activity, from the interface toward the depth direction of the antithrombogenic material, and finding atoms derived from the coating material at a position deeper than a position where atoms derived from the base material are found. For example, when the base material is a polyester or ePTFE, the presence of the coating material can be confirmed by finding nitrogen atoms derived from the polymer and/or sulfur atoms derived from the anionic compound containing a sulfur atom and having anticoagulant activity, at a position deeper than a position where oxygen atoms, fluorine atoms and/or the like derived from the base material are found. The interface of the base material herein means the position in the depth direction where the atoms derived from the base material are found. The presence of each kind of atoms is judged based on whether a peak intensity derived from the atoms can be found in a spectrum obtained by STEM measurement after subtraction of the background.

Atoms derived from the coating material, which is the polymer and the anionic compound containing a sulfur atom and having anticoagulant activity, are present at positions more distant from the interface of the antithrombogenic material in the depth direction from the position of the interface of the base material. More specifically, nitrogen atoms and sulfur atoms are preferably present to a depth of at least 20 to 100 nm, more preferably present to a depth of 50 to 90 nm, from the interface of the base material. We found that when the coating material is present to a depth of at least 20 to 100 nm from the interface of the base material, the amount of the anionic compound containing a sulfur atom and having anticoagulant activity eluted and the elution rate of the compound are preferred, and high antithrombogenicity can be maintained for a long period. When the coating material is present to a depth of only less than 50 nm, elution of the anionic compound containing a sulfur atom and having anticoagulant activity occurs too fast, which is not preferred. On the other hand, when the coating material is present to a depth of more than 100 nm, the amount of the compound eluted and the elution rate are preferred, but deterioration of the polyester base material due to hydrolysis caused by the acid or the alkali, and the oxidizing agent, rapidly proceeds, leading to a decrease in mechanical properties of the base material such as the tensile strength, which is not preferred. In a base material which is not a porous material having pores, the coating material is preferably bound to a depth of 20 to 100 nm.

EXAMPLES

Our materials and methods are described below in detail by way of Examples and Comparative Examples. However, this disclosure is not limited thereto.

Example 1

A PET mesh (diameter, 27 μm; interfiber distance, 100 μm) as a base material was immersed in an aqueous solution of 5.0 wt % potassium permanganate (manufactured by Wako Pure Chemical Industries, Ltd.) and 0.6 mol/L sulfuric acid (manufactured by Wako Pure Chemical Industries, Ltd.), and the reaction allowed to proceed at 60° C. for 3 hours, thereby hydrolyzing and oxidizing the PET mesh (hydrolysis/oxidation step). The aqueous solution after the reaction was removed, and the mesh washed with hydrochloric acid (manufactured by Wako Pure Chemical Industries, Ltd.) and distilled water.

Subsequently, the PET mesh was immersed in an aqueous solution of 0.5 wt % DMT-MM (manufactured by Wako Pure Chemical Industries, Ltd.) and 5.0 wt % PEI (LUPASOL (registered trade mark) P, manufactured by BASF), which is a part of the coating material, and the reaction was allowed to proceed at 30° C. for 2 hours, thereby covalently binding PEI to the PET mesh by condensation reaction (first coating step). The aqueous solution after the reaction was removed, and the mesh was washed with distilled water.

The PET mesh was further immersed in 1 wt % aqueous methanol solution of ethyl bromide (manufactured by Wako Pure Chemical Industries, Ltd.) or pentyl bromide (manufactured by Wako Pure Chemical Industries, Ltd.), and the reaction was allowed to proceed at 35° C. for 1 hour, and then at 50° C. for 4 hours, thereby allowing modification of PEI covalently bound to the surface of the PET mesh with quaternary ammonium (quaternary-ammonium-modification step). The aqueous solution after the reaction was removed, and the mesh was washed with methanol and distilled water.

Finally, the mesh was immersed in an aqueous solution (pH 4) of 0.75 wt % heparin sodium (manufactured by Organon API Inc.) and 0.1 mol/L sodium chloride, and the reaction was allowed to proceed at 70° C. for 6 hours, thereby allowing ionic bonding with PEI (second coating step). The aqueous solution after the reaction was removed, and the mesh was washed with distilled water.

A PET mesh subjected to the second coating step without performing the quaternary-ammonium-modification step was provided as Sample 1; a PET mesh subjected to the quaternary-ammonium-modification step using ethyl bromide was provided as Sample 2; and a PET mesh subjected to the quaternary-ammonium-modification step using pentyl bromide was provided as Sample 3.

Each sample was subjected to measurement of the surface amount based on the anti-factor Xa activity after 30 minutes of immersion in physiological saline, evaluation by the human whole blood test, and evaluation of hemolytic toxicity. The results are shown in Table 2. As shown in Table 2, Samples 1 to 3 showed large surface amounts according to the measurement based on the anti-factor Xa activity. No thrombus adhesion (−) was observed in the evaluation by the human whole blood test, and the hemolytic toxicity was evaluated as nonhemolytic (−).

Example 2

The first coating step was carried out by the same operation as in Example 1, and the PET mesh then immersed in a solution of 0.5 wt % DMT-MM and 40 wt % succinic anhydride (manufactured by Wako Pure Chemical Industries, Ltd.) in dimethylacetamide, followed by allowing the reaction to proceed at 50° C. for 17 hours (first additional step). The solution after the reaction was removed, and the mesh washed with methanol and distilled water. The PET mesh was then immersed in an aqueous solution of 0.5 wt % DMT-MM and 5.0 wt % PEI, and the reaction allowed to proceed at 30° C. for 2 hours (second additional step). The aqueous solution after the reaction was removed, and the mesh washed with distilled water. The quaternary-ammonium-modification step was carried out using ethyl bromide by the same operation as in Example 1, and the second coating step was then carried out.

A PET mesh subjected to the second additional step using PEI (LUPASOL (registered trade mark) P, manufactured by BASF) was provided as Sample 4, and a PET mesh subjected to the second additional step using PEI (LUPASOL (registered trade mark) SK, manufactured by BASF) was provided as Sample 5.

Each sample was subjected to measurement of the surface amount based on the anti-factor Xa activity after 30 minutes of immersion in physiological saline, evaluation by the human whole blood test, and evaluation of hemolytic toxicity. The results are shown in Table 2. As shown in Table 2, Samples 4 and 5 showed large surface amounts according to the measurement based on the anti-factor Xa activity. No thrombus adhesion (−) was observed in the evaluation by the human whole blood test, and the hemolytic toxicity was evaluated as nonhemolytic (−).

Example 3

The first coating step was carried out by the same operation as in Example 1, and the PET mesh then immersed in an aqueous solution of 0.5 wt % DMT-MM and 0.5 wt % PAA (manufactured by Wako Pure Chemical Industries, Ltd.), followed by allowing the reaction to proceed at 30° C. for 2 hours (first additional step). The aqueous solution after the reaction was removed, and the mesh washed with an aqueous sodium carbonate solution and distilled water.

The PET mesh was then further immersed in an aqueous solution of 0.5 wt % DMT-MM and 5.0 wt % PEI, and the reaction allowed to proceed at 30° C. for 2 hours (second additional step). The aqueous solution after the reaction was removed, and the mesh washed with distilled water. The quaternary-ammonium-modification step was carried out using ethyl bromide by the same operation as in Example 1, and the second coating step then carried out.

A PET mesh subjected to the second additional step using PEI (average molecular weight, about 600; manufactured by Wako Pure Chemical Industries, Ltd.) was provided as Sample 6; a PET mesh subjected to the second additional step using PEI (LUPASOL (registered trade mark) P, manufactured by BASF) was provided as Sample 7; and a PET mesh subjected to the second additional step using poly (allylamine hydrochloride) (hereinafter referred to as "PAH") (weight average molecular weight, 900,000; manufactured by Sigma-Aldrich) was provided as Sample 8.

Each sample was subjected to measurement of the surface amount based on the anti-factor Xa activity after 30 minutes of immersion in physiological saline, evaluation by the human whole blood test, and evaluation of hemolytic toxicity. The results are shown in Table 2. As shown in Table 2, Samples 6 to 8 showed large surface amounts according to the measurement based on the anti-factor Xa activity. No thrombus adhesion (−) was observed in the evaluation by the human whole blood test, and the hemolytic toxicity was evaluated as nonhemolytic (−).

Example 4

The first coating step was carried out by the same operation as in Example 1 except that poly(allylamine hydrochloride) (hereinafter referred to as "PAH") (weight average molecular weight, 900,000; manufactured by Sigma-Aldrich) or poly-L-lysine hydrobromide (hereinafter referred to as PLys) (average molecular weight, 30,000 to 70,000; manufactured by Sigma-Aldrich) was used instead of PEI (LUPASOL (registered trade mark) P, manufactured by BASF). The quaternary-ammonium-modification step was carried out by the same operation as in Example 1 using ethyl bromide, and the second coating step then carried out.

A PET mesh subjected to the first coating step using PAH instead of PEI (LUPASOL (registered trade mark) P, manufactured by BASF) was provided as Sample 9, and a PET mesh subjected to the first coating step using PLys instead of PEI (LUPASOL (registered trade mark) P, manufactured by BASF) was provided as Sample 10.

Each sample was subjected to measurement of the surface amount based on the anti-factor Xa activity after 30 minutes of immersion in physiological saline, evaluation by the human whole blood test, and evaluation of hemolytic toxicity. The results are shown in Table 2. As shown in Table 2, Samples 9 and 10 showed large surface amounts according to the measurement based on the anti-factor Xa activity. No thrombus adhesion (−) was observed in the evaluation by the human whole blood test, and the hemolytic toxicity was evaluated as nonhemolytic (−).

Example 5

A PET mesh was immersed in an aqueous solution of 5% PEI, and irradiated with 5 kGy γ-ray (JS-8500 Cobalt 60 γ-ray irradiator, manufactured by Nordion International Inc.) to allow covalent bonding (first coating step). The aqueous solution after the reaction was removed, and the mesh washed with Triton-X100 (manufactured by Sigma-Aldrich), physiological saline, and distilled water. The quaternary-ammonium-modification step was carried out using ethyl bromide by the same operation as in Example 1, and the second coating step then carried out.

A PET mesh subjected to the first coating step using PEI (LUPASOL (registered trade mark) P, manufactured by BASF) was provided as Sample 11.

Each sample was subjected to measurement of the surface amount based on the anti-factor Xa activity after 30 minutes of immersion in physiological saline, evaluation by the human whole blood test, and evaluation of hemolytic toxicity. The results are shown in Table 2. As shown in Table 2, Sample 11 showed a moderate surface amount according to the measurement based on the anti-factor Xa activity. No thrombus adhesion (−) was observed in the evaluation by the human whole blood test, and the hemolytic toxicity was evaluated as nonhemolytic (−).

Example 6

The second coating step was carried out by the same operation as in Example 1 except that dextran sulfate sodium (Wako Pure Chemical Industries, Ltd.) was used instead of heparin sodium (manufactured by Organon API Inc.), to provide the resulting PET mesh as Sample 12.

Sample 12 was subjected to evaluation by the human whole blood test, and evaluation of hemolytic toxicity. The results are shown in Table 2. As shown in Table 2, no thrombus adhesion (−) was observed in the evaluation by the human whole blood test, and the hemolytic toxicity was evaluated as nonhemolytic (−).

Comparative Example 1

A PET mesh was immersed in an aqueous solution of 5% PEI, and irradiated with 5 kGy γ-ray (JS-8500 Cobalt 60 γ-ray irradiator, manufactured by Nordion International Inc.) to allow covalent bonding (first coating step). The aqueous solution after the reaction was removed, and the mesh washed with Triton-X100 (manufactured by Sigma-Aldrich), physiological saline, and distilled water. The quaternary-ammonium-modification step was carried out using ethyl bromide by the same operation as in Example 1, and the second coating step then carried out.

A PET mesh that was subjected to the first coating step using PEI (average molecular weight, about 600; manufactured by Wako Pure Chemical Industries, Ltd.), but not subjected to the quaternary-ammonium-modification step thereafter, was provided as Sample 13; a PET mesh subjected to the first coating step using PEI (average molecular weight, about 600; manufactured by Wako Pure Chemical Industries, Ltd.) was provided as Sample 14; a PET mesh subjected to the first coating step using PEI (LUPASOL (registered trade mark) SK, manufactured by BASF) was provided as Sample 15; and a PET mesh subjected to the first coating step using PEI (LUPASOL (registered trade mark) P, manufactured by BASF), and then to the second coating step using dextran sulfate sodium (Wako Pure Chemical Industries, Ltd.) was provided as Sample 16.

Each sample was subjected to measurement of the surface amount based on the anti-factor Xa activity after 30 minutes of immersion in physiological saline, evaluation by the human whole blood test, and evaluation of hemolytic toxicity. The results are shown in Table 2. As shown in Table 2, Samples 13 to 16 were evaluated as nonhemolytic (−) in terms of the hemolytic toxicity. However, in the evaluation by the human whole blood test, thrombus adhesion (+) was observed. The surface amount according to the measurement based on the anti-factor Xa activity was small.

Comparative Example 2

A PET mesh was immersed in an aqueous solution of 5% PEI, and heated at 80° C. for 2 hours, thereby covalently binding PEI to the PET mesh by aminolysis reaction (first coating step). The aqueous solution after the reaction was removed, and the mesh washed with distilled water. The quaternary-ammonium-modification step was carried out using ethyl bromide by the same operation as in Example 1, and the second coating step then carried out.

A PET mesh subjected to the first coating step using PEI (average molecular weight, about 600; manufactured by Wako Pure Chemical Industries, Ltd.) was provided as Sample 17; a PET mesh subjected to the first coating step using PEI (LUPASOL (registered trade mark) P, manufactured by BASF) was provided as Sample 18; and a PET mesh subjected to the first coating step using PEI (LUPASOL (registered trade mark) SK, manufactured by BASF) was provided as Sample 19.

Each sample was subjected to measurement of the surface amount based on the anti-factor Xa activity after 30 minutes of immersion in physiological saline, evaluation by the human whole blood test, and evaluation of hemolytic toxicity. The results are shown in Table 2. As shown in Table 2, Samples 17 to 19 were evaluated as nonhemolytic (−) in terms of the hemolytic toxicity. However, in the evaluation by the human whole blood test, thrombus adhesion (+) was observed. The surface amount according to the measurement based on the anti-factor Xa activity was small.

Comparative Example 3

The first coating step was carried out by the same operation as in Example 1 except that PEI (average molecular weight, about 600; manufactured by Wako Pure Chemical Industries, Ltd.) was used instead of PEI (LUPASOL (registered trade mark) P, manufactured by BASF). The quaternary-ammonium-modification step was carried out by the same operation as in Example 1 using ethyl bromide, and the second coating step then carried out. The resulting PET mesh was provided as Sample 20.

Sample 20 was subjected to measurement of the surface amount based on the anti-factor Xa activity after 30 minutes of immersion in physiological saline, evaluation by the human whole blood test, and evaluation of hemolytic toxicity. The results are shown in Table 2. As shown in Table 2, Samples 20 was evaluated as nonhemolytic (−) in terms of the hemolytic toxicity. However, in the evaluation by the human whole blood test, thrombus adhesion (+) was observed. The surface amount according to the measurement based on the anti-factor Xa activity was small.

Comparative Example 4

The first coating step was carried out by the same operation as in Example 1, and the PET mesh then immersed in an aqueous solution of 0.5 wt % DMT-MM and 0.5 wt % PAA (manufactured by Wako Pure Chemical Industries, Ltd.), followed by allowing the reaction to proceed at 30° C. for 2 hours (first additional step). The aqueous solution after the reaction was removed, and the mesh washed with an aqueous sodium carbonate solution and distilled water.

The PET mesh was then further immersed in an aqueous solution of 0.5 wt % DMT-MM and 5.0 wt % PEI, and the reaction allowed to proceed at 30° C. for 2 hours (second additional step). The aqueous solution after the reaction was removed, and the mesh washed with distilled water.

The PET mesh was then further immersed in an aqueous solution of 0.5 wt % DMT-MM and 0.5 wt % PAA (Wako Pure Chemical Industries, Ltd.), and the reaction allowed to proceed at 30° C. for 2 hours (third additional step). The aqueous solution after the reaction was removed, and the mesh washed with an aqueous sodium carbonate solution and distilled water.

The PET mesh was then further immersed in an aqueous solution of 0.5 wt % DMT-MM and 5.0 wt % PEI, and the reaction allowed to proceed at 30° C. for 2 hours (fourth additional step). The aqueous solution after the reaction was removed, and the mesh washed with distilled water. The quaternary-ammonium-modification step was carried out by the same operation as in Example 1 using ethyl bromide, and the second coating step then carried out.

A PET mesh subjected to the fourth additional step using PEI (LUPASOL (registered trade mark) P, manufactured by BASF) was provided as Sample 21, and a PET mesh subjected to the fourth additional step using PEI (LUPASOL (registered trade mark) SK, manufactured by BASF) was provided as Sample 22.

Each sample was subjected to measurement of the surface amount based on the anti-factor Xa activity after 30 minutes of immersion in physiological saline, evaluation by the human whole blood test, and evaluation of hemolytic toxicity. The results are shown in Table 2. As shown in Table 2, Samples 21 and 22 showed large surface amounts according to the measurement based on the anti-factor Xa activity. No thrombus adhesion (−) was observed in the evaluation by the human whole blood test. The hemolytic toxicity was evaluated as mildly hemolytic (+).

Example 7

The same operation as in Example 1 was carried out except that a PET film was used as the base material. A PET film subjected to the second coating step without performing the quaternary-ammonium-modification step, similarly to Sample 1, was provided as Sample 23; a PET film subjected to the quaternary-ammonium-modification step using ethyl bromide, similarly to Sample 2, was provided as Sample 24; and a PET mesh subjected to the quaternary-ammonium-modification step using pentyl bromide, similarly to Sample 3, was provided as Sample 25. Samples 23 to 25 were subjected to evaluation by a cellular adhesiveness test. The results are shown in Table 3. As shown in Table 3, Samples 23 to 25 were evaluated as (++) in terms of cellular adhesiveness.

Example 8

The same operation as in Example 3 was carried out except that a PET film was used as the base material. The PET film was subjected to the second additional step using PEI (LUPASOL (registered trade mark) P, manufactured by BASF) similarly to Sample 7, to provide Sample 26. Sample 26 was subjected to evaluation by the cellular adhesiveness test. The results are shown in Table 3. As shown in Table 3, Sample 26 was evaluated as (+) in terms of cellular adhesiveness.

Example 9

The same operation as in Example 5 was carried out except that a PET film was used as the base material. The PET film was subjected to the first coating step using PEI (LUPASOL (registered trade mark) P, manufactured by BASF) similarly to Sample 11, to provide Sample 27. Sample 27 was subjected to evaluation by the cellular adhesiveness test. The results are shown in Table 3. As shown in Table 3, Sample 27 was evaluated as (++) in terms of cellular adhesiveness.

Comparative Example 5

The same operation as in Comparative Example 1 was carried out except that a PET film was used as the base material. A PET film that was subjected to the first coating step using PEI (average molecular weight, about 600; manufactured by Wako Pure Chemical Industries, Ltd.), but not subjected to the quaternary-ammonium-modification step thereafter, similarly to Sample 13, was provided as Sample 28; and a PET film that was subjected to the first coating step using PEI (average molecular weight, about 600; manufactured by Wako Pure Chemical Industries, Ltd.), similarly to Sample 14, was provided as Sample 29. Samples 28 and 29 were subjected to evaluation by the cellular adhesiveness test. The results are shown in Table 3. As shown in Table 3, Samples 28 and 29 were evaluated as (++) in terms of cellular adhesiveness.

Comparative Example 6

The same operation as in Comparative Example 4 was carried out except that a PET film was used as the base material. A PET film subjected to the fourth additional step using PEI (LUPASOL (registered trade mark) P, manufactured by BASF), similarly to Sample 21, was provided as Sample 30, and a PET film subjected to the fourth additional step using PEI (LUPASOL (registered trade mark) SK, manufactured by BASF), similarly to Sample 22, was provided as Sample 31. Samples 30 and 31 were subjected to evaluation by the cellular adhesiveness test. The results are shown in Table 3. As shown in Table 3, Samples 30 and 31 were evaluated as (−) in terms of cellular adhesiveness.

In relation to antithrombogenicity and safety of the material, the method of evaluation of the surface amount based on the anti-factor Xa activity, the method of evaluation by the human whole blood test, and the method of evaluation of hemolytic toxicity are described below.

In relation to cellular adhesiveness of the material, an evaluation method by the cellular adhesiveness test, in which the amount of adhering cells after culture is measured by the absorbance, is described below.

Evaluation 1: Surface Amount Estimated Based on Anti-Factor Xa Activity

An antithrombogenic material (for example, PET mesh) prepared by coating with a coating material was cut into a piece having a size of 0.5×0.5 cm, and the piece washed with physiological saline at 37° C. for 30 minutes. The washed PET mesh was reacted according to the procedure for "TESTZYM (registered trademark) Heparin S" (manufactured by Sekisui Medical Co., Ltd.), and the absorbance at 405 nm measured using a microplate reader (MTP-300, manufactured by Corona Electric Co., Ltd.), followed by calculating the surface amount based on the anti-factor Xa activity according to the procedure for TESTZYM Heparin S. The higher the surface amount, the better. The surface amount is preferably not less than 25 mIU/cm$^2$, more preferably not less than 50 mIU/cm$^2$.

Evaluation 2: Human Whole Blood Test

An antithrombogenic material (for example, PET mesh) prepared by coating with a coating material, or the same type of base material which is not coated with the coating material (positive control), was cut into a piece having an effective surface area of 1.0 cm$^2$. The piece was washed with physiological saline at 37° C. for 30 minutes, and placed in a 2-mL microtube. After adding Heparin Sodium Injection (manufactured by Ajinomoto Pharmaceuticals Co., Ltd.) to fresh human blood to a concentration of 0.5 U/mL, 2 mL of the resulting human blood was added to the microtube, and the tube then incubated at 37° C. for 2 hours. Thereafter, the mesh was removed, and rinsed with PBS(−) (manufactured by Nissui Pharmaceutical Co., Ltd.), followed by quantifying the weight of thrombi attached. The thrombus weight was determined by measuring the dry weights of the mesh before the test and the mesh after the rinse, and calculating the difference between these weights. Tests were carried out for each of the sample and the positive control, in three replicates. When the mean of the relative values of the thrombus weight calculated according to Equation 3 was not less than 10%, the material was evaluated as having thrombus adhesion (+), while when the mean is less than 10%, the material was evaluated as having no thrombus adhesion (−).

Evaluation 3: Hemolytic Toxicity Test

Fresh human blood was fed into an Erlenmeyer flask containing glass beads, such that the blood flowed along the wall surface of the flask. The flask was then placed on a palm, and horizontally shaken in a circular motion at a rate of about two rotations per second for about 5 minutes, to prepare defibrinated blood. An antithrombogenic material (for example, PET mesh) prepared by coating with a coating material was cut into a piece having a size of 1.0×2.0 cm, and the piece was washed with physiological saline at 37° C. for 30 minutes. The washed piece was placed in a 2-mL microtube. To the microtube containing the mesh, 1 mL of the defibrinated blood after 50-fold dilution with physiological saline was added, and the tube was then incubated at 37° C. for 4 hours. Thereafter, the microtube was centrifuged at 750 G for 5 minutes. The resulting supernatant was collected, and subjected to measurement of the UV absorbance at 576 nm. When the value calculated according to Equation 4 was larger than 2, that is, when the material was hemolytic, the material was evaluated as (+), while when the value was not more than 2, that is, when the material was nonhemolytic, the material was evaluated as (−). Since the material preferably has no hemolytic toxicity, the material is preferably nonhemolytic.

Evaluation 4: Cellular Adhesiveness Test

The cellular adhesiveness is a property indicating a tendency to allow adhesion of cells to a material, and measured by the following evaluation method. Each of Samples 23 to 31 was punched into a disk sample having a diameter of 15 mm using a puncher. Each disk sample was placed in a well of a 24-well microplate for cell culture (manufactured by Sumitomo Bakelite Co., Ltd.) such that the inner-wall side is facing upward, and a metal pipe-shaped weight having a thickness of 1 mm was placed on the top of the sample. To each well, normal human umbilical vein endothelial cells (Takara Bio Inc.) suspended in 2% FBS endothelial cell culture kit-2 (manufactured by Takara Bio Inc.) were added such that the well contained 4×10$^4$ cells. The cells were cultured in 1 mL of a medium at 37° C. under an environment of 5% $CO_2$ for 24 hours. After rinsing the well with PBS(−) (manufactured by Nissui Pharmaceutical Co., Ltd.), 100 μL of Cell Counting Kit-8 (manufactured by Dojindo Laboratories) was added thereto, and the cells cultured at 37° C. under an environment of 5% $CO_2$ for 4 hours. Subsequently, the absorbance at 450 nm was measured using a microplate reader (MTP-300, manufactured by Corona Electric Co., Ltd.), followed by calculation of the absorbance as shown by Equation 5.

$$As = At - Ab \qquad (5)$$

At: measured absorbance
Ab: absorbance of the blank solution (medium, and the solution of Cell Counting Kit-8; containing no cells)
As: absorbance calculated Since the amount of adhering cells after the culture can be known from the calculated absorbance As, a score for cellular adhesiveness was determined based on the absorbance As. More specifically, when As was less than 0.5, the cellular adhesiveness was judged as being weak, and the sample was evaluated as (−); when As was not less than 0.5, the cellular adhesiveness was judged as being strong, and the sample was evaluated as (+); and, when As was not less than 0.7, the cellular adhesiveness was judged as being even stronger, and the sample was evaluated as (++).

TABLE 2

| | Sample | Polymer | Sulfur-containing compound | Abundance ratio of sulfur element (atomic percent) | Abundance ratio of nitrogen element (atomic percent) | Weight average molecular weight | Carbon number of alkyl group (number) | Surface amount according to measurement based on anti-factor Xa activity (mIU/cm$^2$) | Thrombus adhesion | Hemolytic toxicity |
|---|---|---|---|---|---|---|---|---|---|---|
| Example 1 | 1 | PEI | Heparin | 4.0 | 8.3 | 750,000 | 0 | 64.2 | − | − |
| | 2 | PEI | Heparin | 3.8 | 8.2 | 750,000 | 2 | 83.5 | − | − |
| | 3 | PEI | Heparin | 3.9 | 8.0 | 750,000 | 5 | 88.6 | − | − |

TABLE 2-continued

|  | Sample | Polymer | Sulfur-containing compound | Abundance ratio of sulfur element (atomic percent) | Abundance ratio of nitrogen element (atomic percent) | Weight average molecular weight | Carbon number of alkyl group (number) | Surface amount according to measurement based on anti-factor Xa activity (mIU/cm²) | Thrombus adhesion | Hemolytic toxicity |
|---|---|---|---|---|---|---|---|---|---|---|
| Example 2 | 4 | PEI | Heparin | 3.3 | 8.0 | 750,000 | 2 | Not less than 100 | − | − |
|  | 5 | PEI | Heparin | 3.5 | 8.2 | 2,000,000 | 2 | Not less than 100 | − | − |
| Example 3 | 6 | PEI | Heparin | 4.3 | 8.9 | 600 | 2 | Not less than 100 | − | − |
|  | 7 | PEI | Heparin | 3.9 | 9.8 | 750,000 | 2 | Not less than 100 | − | − |
|  | 8 | PAH | Heparin | 3.4 | 6.5 | 900,000 | 2 | 55.4 | − | − |
| Example 4 | 9 | PAH | Heparin | 3.2 | 7.3 | 900,000 | 2 | 52.3 | − | − |
|  | 10 | PLys | Heparin | 3.2 | 7.1 | 300,000 to 700,000 | 2 | 41.5 | − | − |
| Example 5 | 11 | PEI | Heparin | 3.1 | 6.4 | 750,000 | 2 | 25.5 | − | − |
| Example 6 | 12 | PEI | Dextran sulfate | 3.6 | 8.2 | 750,000 | 2 | — | − | − |
| Comparative Example 1 | 13 | PEI | Heparin | 1.0 | 2.5 | 600 | 0 | 3.2 | + | − |
|  | 14 | PEI | Heparin | 1.0 | 2.4 | 600 | 2 | 8.2 | + | − |
|  | 15 | PEI | Heparin | 1.0 | 2.9 | 2,000,000 | 2 | 8.4 | + | − |
|  | 16 | PEI | Dextran sulfate | 2.6 | 5.6 | 750,000 | 2 | — | + | − |
| Comparative Example 2 | 17 | PEI | Heparin | 1.1 | 2.6 | 600 | 2 | 8.8 | + | − |
|  | 18 | PEI | Heparin | 1.1 | 3.4 | 750,000 | 2 | 10.5 | + | − |
|  | 19 | PEI | Heparin | 1.1 | 3.1 | 2,000,000 | 2 | 10.1 | + | − |
| Comparative Example 3 | 20 | PEI | Heparin | 1.4 | 3.4 | 600 | 2 | 15.7 | + | − |
| Comparative Example 4 | 21 | PEI | Heparin | 6.3 | 12.8 | 750,000 | 12 | Not less than 100 | − | + |
|  | 22 | PEI | Heparin | 6.3 | 12.5 | 2,000,000 | 12 | Not less than 100 | − | + |

TABLE 3

|  | Sample | Polymer | Sulfur-containing compound | Abundance ratio of sulfur element (atomic percent) | Abundance ratio of nitrogen element (atomic percent) | Weight average molecular weight | Carbon number of alkyl group (number) | Cellular adhesiveness |
|---|---|---|---|---|---|---|---|---|
| Example 7 | 23 | PEI | Heparin | 4.0 | 8.3 | 750,000 | 0 | ++ |
|  | 24 | PEI | Heparin | 3.8 | 8.2 | 750,000 | 2 | ++ |
|  | 25 | PEI | Heparin | 3.9 | 8.0 | 750,000 | 5 | ++ |
| Example 8 | 26 | PEI | Heparin | 3.9 | 9.8 | 750,000 | 2 | + |
| Example 9 | 27 | PEI | Heparin | 3.1 | 6.4 | 750,000 | 2 | ++ |
| Comparative Example 5 | 28 | PEI | Heparin | 1.0 | 2.5 | 600 | 0 | ++ |
|  | 29 | PEI | Heparin | 1.0 | 2.4 | 600 | 2 | ++ |
| Comparative Example 6 | 30 | PEI | Heparin | 6.3 | 12.8 | 750,000 | 12 | − |
|  | 31 | PEI | Heparin | 6.3 | 12.5 | 2,000,000 | 12 | − |

INDUSTRIAL APPLICABILITY

The antithrombogenic material can be used for medical equipment and medical instruments requiring maintenance of high antithrombogenicity for a long period, in the field of medicine.

The invention claimed is:

1. An antithrombogenic material comprising:
a coating material containing:
a polymer containing, as a constituent monomer, a compound selected from the group consisting of alkyleneimines, vinylamines, allylamines, lysine, protamine and diallyldimethylammonium chloride; and
an anionic compound containing a sulfur atom and having anticoagulant activity; and
a base material whose surface is coated with said coating material;
wherein
said polymer is covalently bound to said base material; and
an abundance ratio of nitrogen atoms to an abundance of total atoms as measured by X-ray photoelectron spectroscopy (XPS) on a surface coated with the coating material is 6.0 to 12.0 atomic percent,
an abundance ratio of sulfur atoms to the abundance of total atoms as measured by X-ray photoelectron spectroscopy (XPS) on the surface coated with the coating material is 3.0 to 6.0 atomic percent, and
a surface amount estimated based on anti-factor Xa activity after immersion in physiological saline for 30 minutes is not less than 30 mIU/cm².

2. The antithrombogenic material according to claim 1, wherein said polymer has a quaternary ammonium group.

3. The antithrombogenic material according to claim 2, wherein each carbon chain bound to the nitrogen atom in said quaternary ammonium group is constituted by an alkyl group, and the carbon number per alkyl group is 1 to 12.

4. The antithrombogenic material according to claim 1, wherein said coating material further comprises:
an anionic polymer containing, as a constituent monomer, a compound selected from the group consisting of acrylic acid, methacrylic acid, α-glutamic acid, γ-glutamic acid and aspartic acid; or an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid and citric acid.

5. The antithrombogenic material according to claim 1, wherein said anionic compound containing a sulfur atom and having anticoagulant activity is heparin or a heparin derivative.

6. The antithrombogenic material according to claim 1, wherein weight average molecular weight of said polymer is 600 to 2,000,000.

7. The antithrombogenic material according to claim 4, wherein weight average molecular weight of said anionic polymer is 600 to 2,000,000.

8. The antithrombogenic material according to claim 1, wherein the abundance ratio of the n2 component as a split peak of nitrogen atoms to a total component of the N1s peak as measured by X-ray photoelectron spectroscopy (XPS) on the surface of the base material is 20 to 70 atomic percent.

9. The antithrombogenic material according to claim 1, wherein an abundance ratio of the c3 component as a split peak of carbon atoms to a total component of the C1s peak as measured by X-ray photoelectron spectroscopy (XPS) on the surface coated with the coating material is not less than 2.0 atomic percent.

10. The antithrombogenic material according to claim 1, wherein said coating material has a mean thickness of 1 to 600 nm.

11. The antithrombogenic material according to claim 1, wherein nitrogen atoms and sulfur atoms in said coating material are located at a distance of 20 to 100 nm away from an interface between said coating material and said base material.

* * * * *